(12) United States Patent
Triplett

(10) Patent No.: US 7,887,759 B2
(45) Date of Patent: Feb. 15, 2011

(54) FRAGRANCE DELIVERY SYSTEM

(75) Inventor: Carl Triplett, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 11/817,893

(22) PCT Filed: Mar. 28, 2006

(86) PCT No.: PCT/US2006/011775

§ 371 (c)(1),
(2), (4) Date: Mar. 17, 2008

(87) PCT Pub. No.: WO2006/105347

PCT Pub. Date: Oct. 5, 2006

(65) Prior Publication Data

US 2008/0279730 A1    Nov. 13, 2008

Related U.S. Application Data

(60) Provisional application No. 60/594,322, filed on Mar. 29, 2005.

(51) Int. Cl.
*A61L 9/00* (2006.01)

(52) U.S. Cl. ........................................ 422/120; 422/123

(58) Field of Classification Search ................. 422/120, 422/123
See application file for complete search history.

(56) References Cited

U.S. PATENT DOCUMENTS

| | | | | |
|---|---|---|---|---|
| 5,364,027 A | * | 11/1994 | Kuhn | ........................... 239/44 |
| 6,209,252 B1 | * | 4/2001 | McGough | ......................... 43/1 |
| 6,610,254 B1 | * | 8/2003 | Furner et al. | ................. 422/123 |
| 6,672,129 B1 | | 1/2004 | Frederickson et al. | |
| 6,790,408 B2 | * | 9/2004 | Whitby et al. | .................. 422/4 |
| 6,950,607 B2 | * | 9/2005 | Yip et al. | ..................... 392/395 |

FOREIGN PATENT DOCUMENTS

FR    2647678 A1 * 12/1990
WO   WO 2004/020002    3/2004

OTHER PUBLICATIONS

International Search Report dated Aug. 1, 2006.

\* cited by examiner

*Primary Examiner*—Sean E Conley
(74) *Attorney, Agent, or Firm*—Snell & Wilmer L.L.P.

(57) ABSTRACT

Multiple delivery vapor dispensing mechanisms provide continuous fragrance release and supplemental on-demand fragrance releases with a portion of the on-demand fragrance releases being deposited to provide for a prolonged elevated fragrance intensity.

7 Claims, 5 Drawing Sheets

FRAGRANCE DELIVERY SYSTEM

FIELD OF INVENTION

The present invention pertains generally to vapor dispensing devices and more particularly to air fresheners having multiple fragrance release mechanisms and various features of the same.

BACKGROUND OF THE INVENTION

Fragrance delivery systems are often described using terms such as "passive," "active," "continuous" or "burst." As used herein, a passive system is one which delivers fragrance without the need for additional energy input to the system (e.g. ambient evaporation). In contrast, active systems require additional energy input, typically in the form of heating elements or fans (e.g. forced evaporation). Burst systems provide an instantaneous increase in fragrance intensity, for example, in the form of an aerosol or spray release. Any of the above systems may be further described as "continuous" or "on-demand." For example, a passive or active delivery, by evaporation or other means, may be either continuous—requiring no initiation—or may be periodically initiated on-demand. Fragrance bursts are typically released on-demand. As used herein, the term "elevated intensity" is relative to the intensity provided by a single continuous delivery system and the terms "prolonged" or "prolonged intensity" are relative to the shorter-lived dissipation of purely atmospheric burst dispersions.

That being said, vapor-dispensing products typically include a volatizable material and a transport system configured to facilitate evaporation of the volatizable material into the surrounding air. Such volatizable materials include fragrances, air fresheners, deodorizers, odor eliminators, odor counteractants, insecticides, insect repellants, medicinal substances, disinfectants, sanitizers, mood enhancers, and aroma therapy compositions. Air fresheners are common exemplary vapor-dispensing devices and are often classified as passive, active or burst fresheners. Continuous passive release fresheners serve to provide a substantially constant fragrance intensity over extended periods and typically include a reservoir and a wick or other evaporative pathway and may include rudimentary intensity controls. Active fresheners, on the other hand, often employ heating elements and/or fans and may thus provide increased control and/or an increased range of fragrance intensity.

Burst fresheners are typically designed to provide instantaneous dispersions, for example, to combat transient or elevated odor levels, and lack the prolonged effect provided by continuous systems. Conventional burst systems employ aerosol propellants or mechanical type pumps and spray nozzles to create dispersions that typically dissipate quickly in the air. Alone, burst dispersions are short lived, characterized by a marked instantaneous increase in intensity followed by relatively rapid dissipation. As such, previous single-delivery systems are inadequate, leaving consumers to choose between passive, active, or burst products or to use multiple products resulting in mixing of different fragrances.

More recent systems have proposed combinations between basic continuous (passive or active) delivery mechanisms and burst delivery mechanisms. Such systems may thus provide either a continuous fragrance release with optional on-demand burst releases, or, on-demand burst releases with a supplemental passive release. So called combined continuous-burst dispensers provide but short-lived burst dispersions in addition to a continuous dispersion. In contrast, combined burst-semi-continuous dispensers provide short-lived atmospheric dispersions with subsequent temporary passive delivery but without any continuous delivery mechanism. Accordingly, such proposed systems lack means of providing a prolonged elevated fragrance intensity between and in addition to the two intensity extremes of their basic continuous and burst system progenitors.

Conventional products do not offer both supplemental burst releases and supplemental passive or active release in addition to a continuous fragrance release. Likewise, such conventional products do not provide prolonged, elevated fragrance release in addition to continuous fragrance release through a supplemental, on-demand passive or active delivery mechanism. Thus, there is a need for a vapor-dispensing device that overcomes these and other limitations of the prior art.

SUMMARY OF THE INVENTION

While the way in which the present invention addresses the disadvantages of the prior art will be discussed in greater detail below, in general, various embodiments of the present invention provide on-demand prolonged elevated fragrance release in addition to continuous fragrance release. Various embodiments include the combined functionality of both continuous and on-demand systems having common or complementary fragrances in common or separate reservoirs. Various embodiments also provide increased control over the intensity and duration of fragrance releases.

An exemplary multiple-delivery fragrance system is any air freshener that provides continuous fragrance release with supplemental on-demand fragrance release such that the plotted settling of fragrance intensity between on-demand releases is substantially prolonged relative to that settling associated with a lone atmospheric burst fragrance release. This gradual settling or decreased rate of dissipation can be adjusted by varying the system burst volume and supplemental release deposits and/or capacities. Likewise, the user may vary the effect manually by repeated on-demand deliveries or by adjusting the portions of bursts delivered immediately into the air versus that portion that is deposited for subsequent release.

An exemplary air freshener in accordance with the present invention comprises at least one reservoir with a first continuous fragrance delivery mechanism and a second on-demand fragrance delivery mechanism drawing on either the first or a second reservoir to provide supplemental prolonged fragrance delivery in addition to the first continuous fragrance delivery. The continuous delivery mechanism includes a mechanism providing substantially constant release of fragrance reserves, such as a wick or emanator. The on-demand delivery mechanism includes a mechanism for dispensing an on-demand burst of fragrance. For example, in one embodiment, a microsprayer deposits at least a portion of the on-demand delivered fragrance onto an emanator for subsequent passive or active fragrance release. Exemplary emanators include any absorbent pad, evaporation surface, porous material or the like. By delaying the release of the deposited fragrance, the overall fragrance intensity is elevated for a prolonged period.

An alternative exemplary air freshener includes a first continuous delivery mechanism and a second on-demand passive emanator. The first emanator is wetted by wicking from a reservoir. The second emanator is saturated on demand, for example by pumping from a reservoir. Such dual delivery embodiments may include common or separate reservoirs having common or complementary fragrances. Exemplary on-demand delivery mechanisms comprise microsprayers, pumps, spritzers and the like.

An exemplary multiple delivery fragrance system includes a continuous delivery mechanism and an on-demand delivery mechanism stocking a supplemental fragrance carrier. Variations of this system include an emanator supplied by continuous communication with a reservoir and an on-demand delivery mechanism for further stocking the same or a second emanator from the same or a second reservoir. The on-demand delivery mechanism may deliver fragrance to an emanator in bursts.

Another embodiment includes an integrated multiple delivery fragrance system having a continuous delivery mechanism, delivering a first fragrance and an on-demand delivery mechanism for delivering periodic fragrance bursts of a second fragrance, wherein at least a portion of the fragrance bursts is deposited on an emanator for subsequent passive delivery. The on-demand delivery mechanism may be a microsprayer and may draw the first and second fragrances from a common reservoir or from separate reservoirs.

In yet another embodiment, a multiple delivery fragrance system includes a continuous delivery mechanism causing a first constant fragrance intensity; and an on-demand delivery mechanism supplementing the first continuous delivery mechanism to cause a second prolonged elevated fragrance intensity. The continuous delivery mechanism includes a first emanator supplied by wicking from a reservoir; and the on-demand delivery mechanism includes a second emanator adjacent the first emanator with a barrier therebetween and a microsprayer for supplying periodic fragrance bursts to the second emanator. In a variation of this embodiment, the continuous delivery mechanism includes a first emanator, wettable by wicking from a first reservoir, and the on-demand delivery mechanism includes a second emanator, wettable on-demand from a second reservoir, for example by pumping, immersion, conduit transport, spray from a nozzle or other suitable wetting action.

Any of the reservoirs in any embodiment may be independently refillable, independently replaceable, or jointly replaceable. The deliverable materials, e.g., fragrances, may be of different scent or types and may be drawn from any number of reservoirs. Likewise, the deliverable materials in any embodiment include fragrances, air fresheners, deodorizers, odor eliminators, insecticides, insect repellants, medicine, disinfectants, sanitizers, mood enhancers, and/or aroma therapy compositions. Any of the embodiments described herein may include a heater, blower, fan, timer, intensity control, duration control and/or sensor.

BRIEF DESCRIPTION OF THE DRAWINGS

The subject invention will hereinafter be described in conjunction with the appended drawing figures, wherein like numerals denote like elements, and.

DETAILED DESCRIPTION

The following description is of exemplary embodiments of the invention only, and is not intended to limit the scope, applicability or configuration of the invention in any way. Rather, the following description is intended to provide a convenient illustration for implementing various embodiments of the invention. As will become apparent, various changes may be made in the function and arrangement of the elements described in these embodiments without departing from the scope of the invention as set forth herein. Generally speaking, various volatizable materials such as insect repellants, deodorizers, sanitizers, and/or the like are suitable for use in accordance with the present invention. It should be appreciated that the description herein may likewise be adapted to be employed with alternatively configured devices having different shapes, components, delivery mechanisms and the like and still fall within the scope of the present invention.

An exemplary air freshener according to the present invention comprises a continuous-passive fragrance delivery mechanism such as a wick and emanator with a supplemental mechanism for providing a fragrance burst and additional prolonged passive fragrance release. An exemplary supplemental mechanism includes a nozzle for delivering a burst of fragrance into the air while depositing additional fragrance on a passive emanator for delayed release. The continuous and supplemental delivery mechanisms can draw fragrance reserves from a common reservoir or from separate reservoirs containing the same or complementary fragrances. Supplemental delivery mechanisms may be either passive, active, burst or any combination of the same.

Describing an exemplary air freshener in terms of performance characteristics, a continuous passive fragrance delivery mechanism provides a substantially constant fragrance intensity. The supplemental fragrance microsprayer provides a substantially instantaneous increase in intensity from an airborne burst. The supplemental fragrance released and/or deposited by the microsprayer in combination with the continuous passive fragrance provides a prolonged elevated fragrance intensity, prolonged being relative to the dissipation of an airborne fragrance burst alone. This embodiment provides supplemental fragrance delivery in a continuous air freshener prolonging the effects of the supplemental delivery by depositing a portion of the delivered supplemental fragrance for delayed passive delivery.

Figure 1:
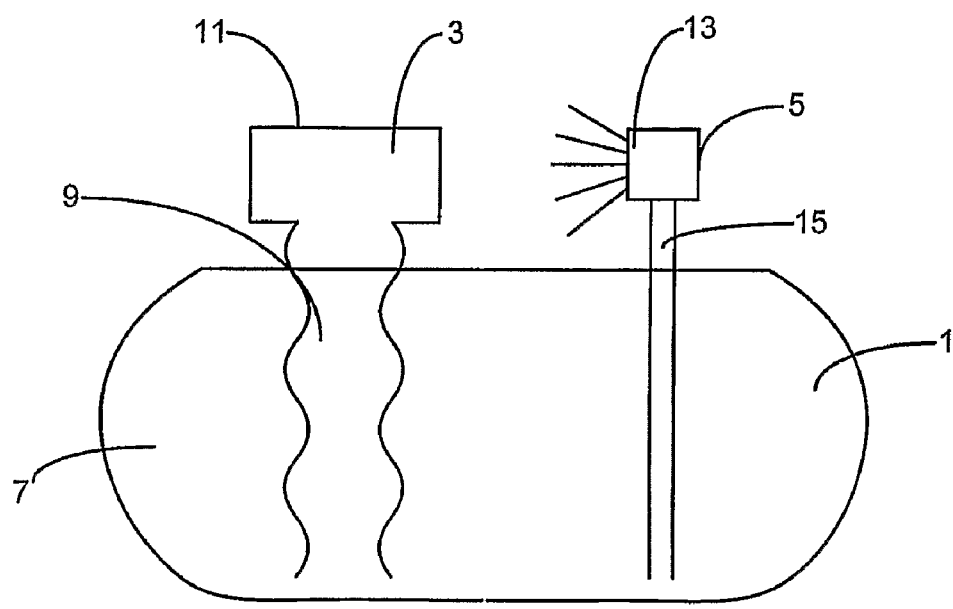
FIG. 1 is an air freshener in accordance with an exemplary embodiment of the present invention showing both continuous passive and on-demand delivery mechanisms.

Referring now to the drawings, FIG. 1 illustrates an air freshener 1 in accordance with an exemplary embodiment of the present invention showing both a continuous delivery mechanism 3 and an on-demand delivery mechanism 5 drawing from a reservoir 7. Continuous delivery mechanism 3 comprises a wick 9 supplying an emanator 11 from reservoir 7. On-demand delivery mechanism 5 comprises a spray nozzle 13 and a conduit 15 supplying spray nozzle 13 from reservoir 7. Spray nozzle 13 comprises a micro-sprayer, for delivering a small fragrance dose. Alternatively, spray nozzle 13 may comprise an atomizer, spritzer, sprayer, pump, nozzle, or any other suitable dispenser. A portion of fragrance bursts from spray nozzle 13 is deposited on emanator 11 and a portion is dispersed immediately into the air. Emanator 11 may have different sections for saturation by constant delivery mechanism 3 and on-demand delivery mechanism 5. On-demand delivery mechanism 5 may, instead, deposit fragrance bursts on an emanator or surface other than emanator 11 supplied by wick 9. For example, a second emanator, backsplash or evaporation surface adjacent emanator 11 may likewise receive on-demand fragrance bursts.

With reference to FIGS. 1-4, and in accordance with various exemplary embodiments of the present invention, emanator 11 is a pad configured from a porous material and having an enlarged surface area. Emanator 11 may, however, be readily substituted with any material or surface capable of storage and release of fragrance reserves. For example, emanator 11 may be an extended portion of wick 9 or may be a surface in contact with wick 9. Emanator 11 and/or wick 9 comprise materials including nylon, porous plastics, various natural and synthetic fibers or other suitable materials.

Air freshener 1 utilizes any suitable fragrance reserves such as, for example, scented water, oil, alcohol, gel, solids or membrane type fragrance reserves. It should be appreciated that any fragrance delivery mechanism now known or later developed in the art can suitably be configured to be used in the present invention.

An exemplary active air freshener 1 may include a heating element and variable temperature control to increase or decrease the amount of fragrance dispensed depending on the heat provided by the heating element, user desired performance, room size and the like. Likewise, an exemplary air freshener 1 may include a blower, fan, timer or detector. Detectors or sensors may be capable of detecting motion, heat, light, fragrance intensity, humidity or other changing conditions as a means of initiating the continuous or on-demand delivery mechanisms.

Figure 2:
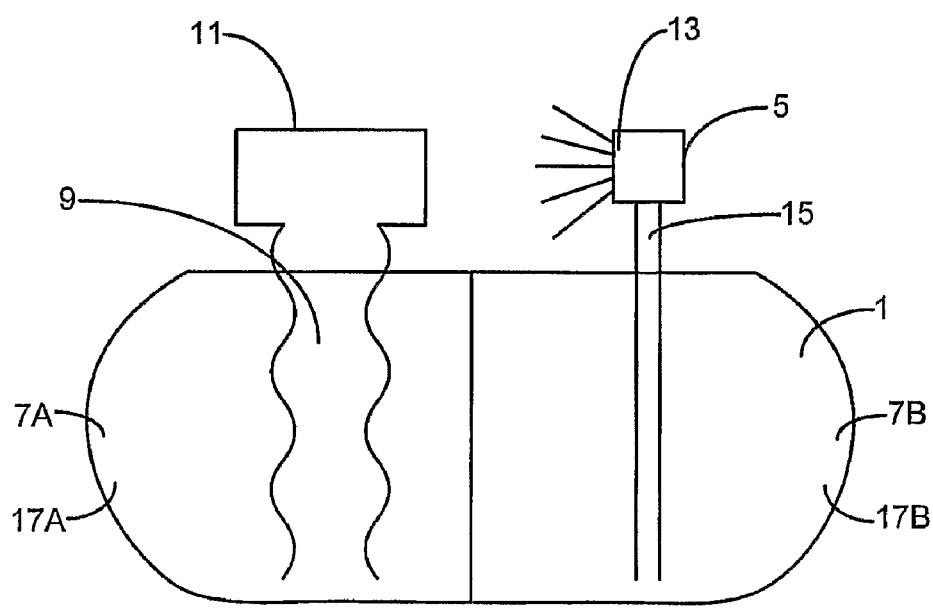
FIG. 2 is an air freshener in accordance with an exemplary embodiment of FIG. 1, showing separate reservoirs.

With reference to FIG. 2, air freshener 1 is shown with two reservoirs 7A and 7B. Reservoirs 7A and 7B may contain similar, different, or complementary fragrances 17A and 17B. Reservoirs 7A and 7B may be single use, refillable, or may comprise removable containers. Accordingly, customers may choose between single fragrance release, overlapping complementary fragrance releases, and may change combinations by selection of alternate fragrance refills. For example, a first fragrance may be constantly dispersed into the environment with a second fragrance for on-demand dispersion. Alternatively, the first and second fragrance reserves may be interchangeable to provide the inverse relationship. Conversely, passive delivery mechanism 3 and on-demand delivery mechanism 5 may be interchangeable between reservoirs 7A and 7B. It is understood that any number of components may readily be rearranged or substituted without departing from the present invention.

Figure 3:
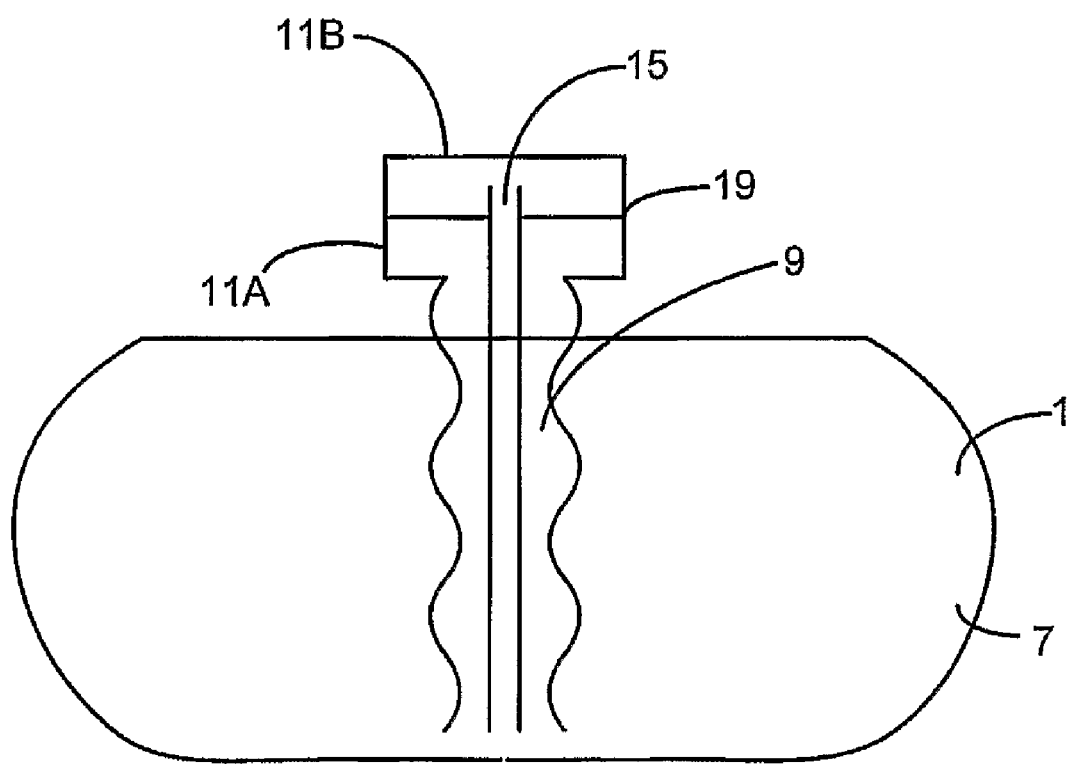
FIG. 3 is an air freshener in accordance with an exemplary embodiment of the present invention, showing an emanator pad with separate continuous passive and on-demand passive sections.

Additionally, in accordance with various embodiments and with particular reference to FIG. 3 components may be integrated to serve multiple functions. For example, air freshener 1 may have two emanators 11A and 11B separated by a barrier 19. Emanator 11A is constantly supplied by wick 9 from reservoir 7. Emanator 11B is supplied on-demand by conduit 15 from reservoir 7. Barrier 19 prevents saturation of emanator 11B by delivery of fragrance bulk to emanator 11A by wick 9. Likewise, barrier 19 prevents seepage to emanator 11A of on-demand deposits to emanator 11B. Emanators 11A and 11B and barrier 19 may, likewise, be oriented vertically. Alternatively, metering of flow from wick 9 may facilitate a unitary emanator 11 for both continuous and supplemental fragrance release. This exemplary configuration allows for compact designs and for centered location of any pump or other mechanism. Emanator 11B is configured to provide the desired supplemental fragrance duration and intensity and may be integral with or separate from passive delivery mechanism 3

Transport through conduit 15 is readily accomplished by any number of means. For example, mechanical pumping action facilitates transport through conduit 15. Alternatively, a flexible sided reservoir 7 may facilitate transport through conduit 15 by application of pressure to reservoir 7. Aerosol or other propellants may likewise be utilized, particularly in connection with on-demand delivery mechanism 5.

Emanator 11 or any similar fragrance depository or carrier may be stocked by multiple on-demand bursts to provide varying intensity levels or duration. Exemplary emanators 11 include wick pads, splash surfaces, deflectors, porous substrates, or pooling recesses. An alternative exemplary embodiment includes an emanator 11 wettable by wicking action from reservoir 7, and a second emanator 11 wettable by momentary submersion in reservoir 7.

Figure 4:
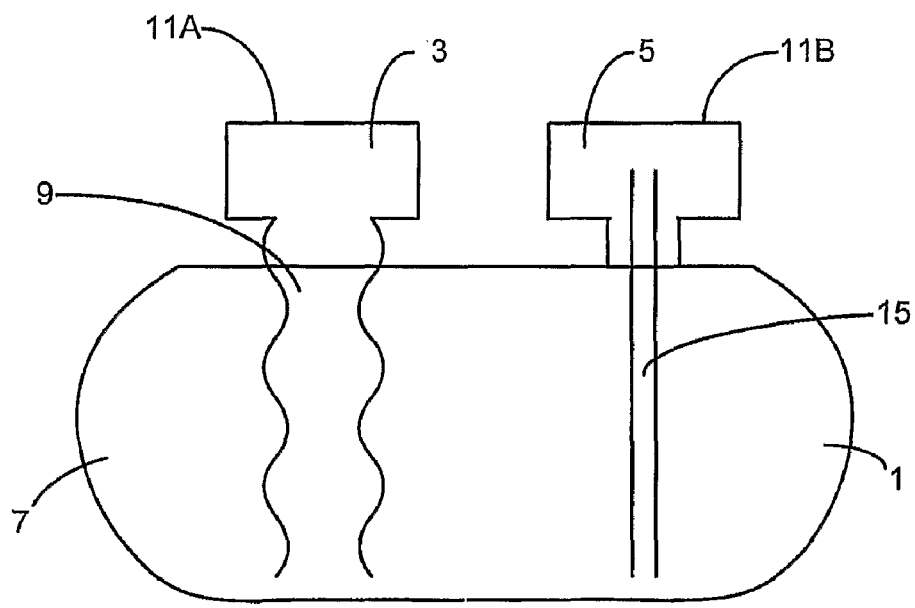
FIG. 4 is an air freshener in accordance with an exemplary embodiment of the present invention, showing separate continuous and on-demand passive emanators.
Figure 5:
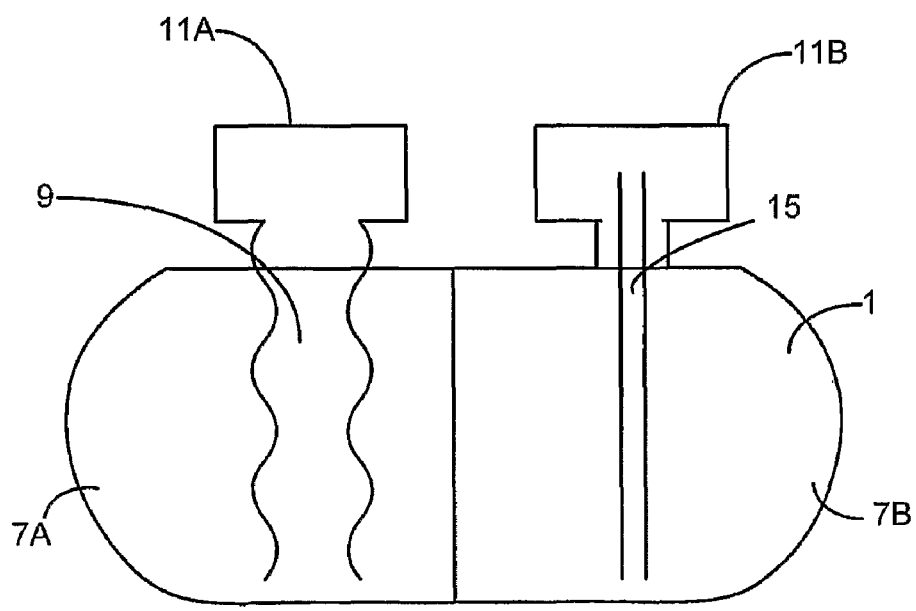
FIG. 5 is an air freshener in accordance with an alternative exemplary embodiment of FIG. 4, showing separate reservoirs.

Turning now to FIGS. 4-5, air freshener 1 includes a continuous passive delivery mechanism 3 and on-demand passive delivery mechanism 5 drawing from reservoir 7 or separate reservoirs 7A and 7B. Continuous passive delivery mechanism 3 may include a conventional wick 9 for transporting liquid fragrance reserves. Alternatively, continuous passive delivery mechanism 3 includes fragrance release from solid or gel fragrance bulk material. Exemplary embodiments provide two different levels of passive fragrance intensity, one caused by continuous fragrance delivery and another caused by combined continuous and supplemental fragrance release.

Figure 6A:
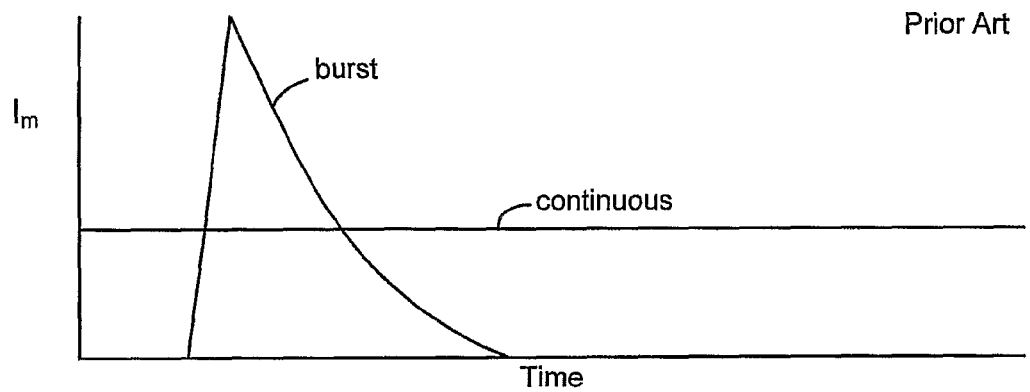
FIG. 6 shows plots of the mean intensities produced by various prior art air fresheners.
Figure 6B:
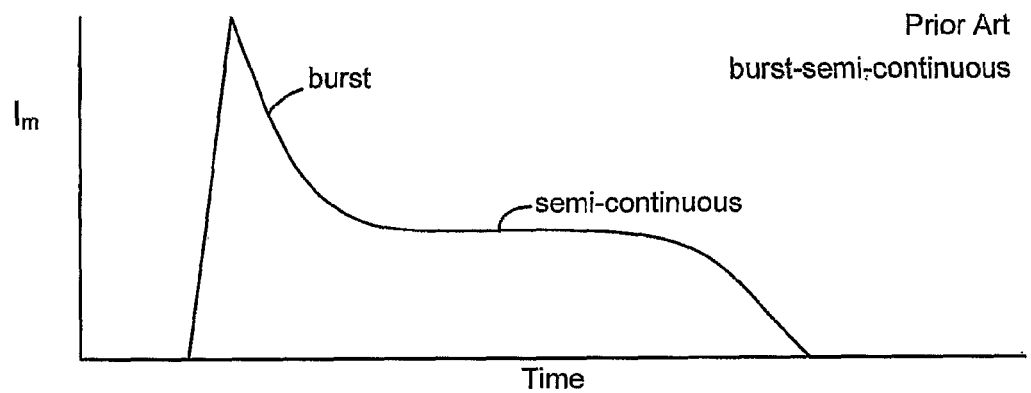
Figure 6C:
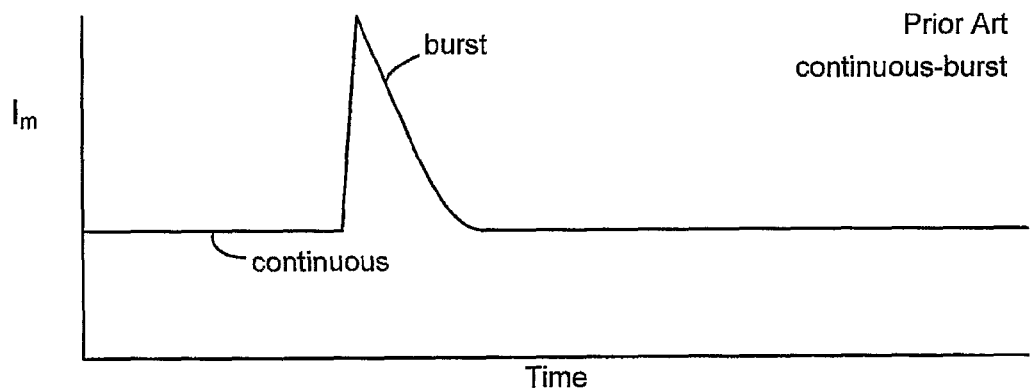

As described above, the embodiments of the present invention achieve different performance properties than the prior art. FIG. 6 shows exemplary plots of various prior art air freshener intensities over time. FIG. 6A shows exemplary performance curves of conventional single delivery continuous and burst air fresheners. FIG. 6B shows an exemplary performance curve of a known burst-semi-continuous air freshener. FIG. 6B shows an exemplary performance curve of a known continuous-burst air freshener.

Figure 7:
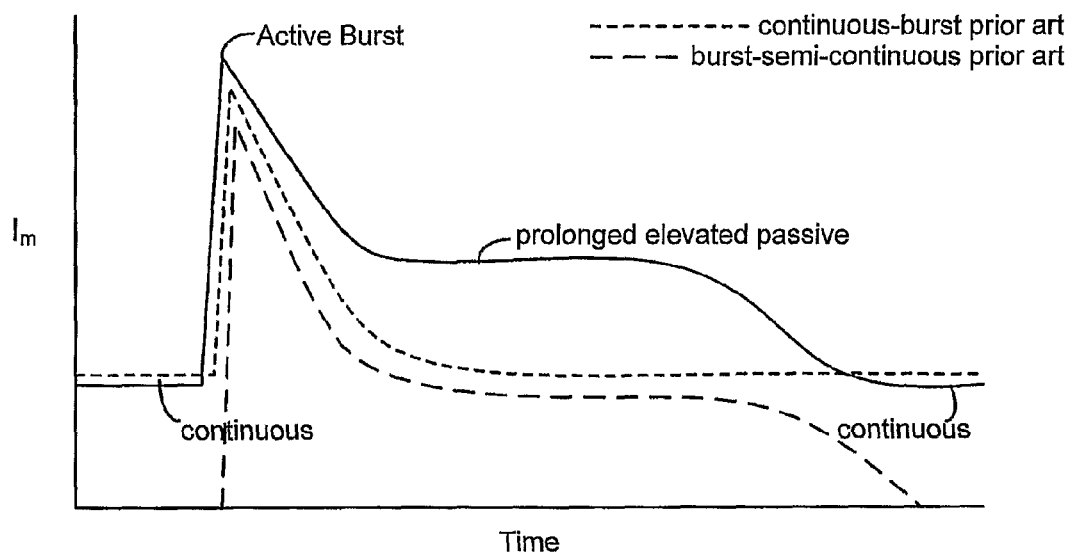
FIG. 7 is a plot of the mean intensity produced by an air freshener in accordance with an exemplary embodiment of the present invention, showing continuous, and supplemental on-demand fragrance mean intensities as compared to prior art intensities.
Figure 8:
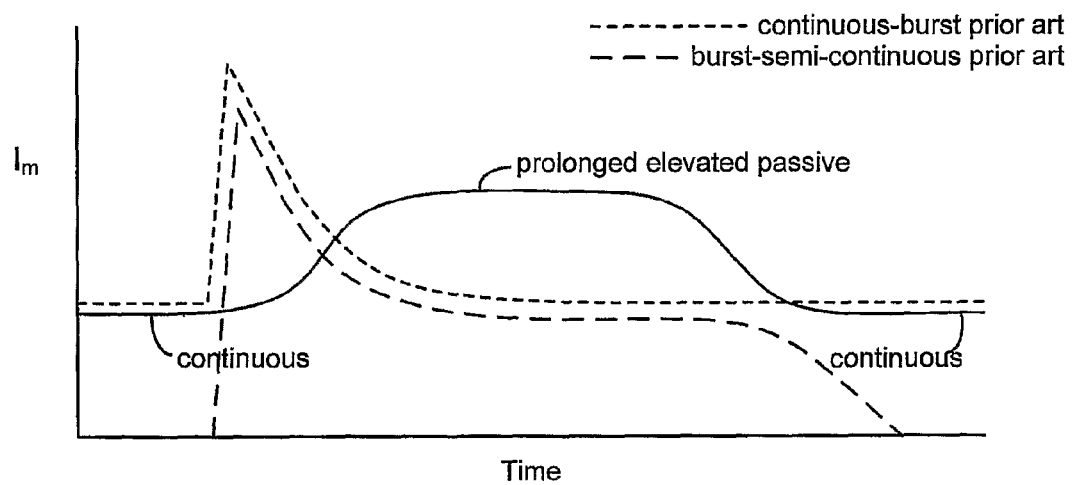
FIG. 8 is a plot of the mean intensity produced by an air freshener in accordance with an alternative exemplary embodiment of the present invention, showing continuous passive and supplemental on-demand passive fragrance mean intensities as compared to prior art fragrance intensities.

FIGS. 7-8 show plots of mean intensity levels within a space surrounding an air freshener according to various embodiments presented in FIGS. 1-5 (solid lines) as compared to prior art performance (dashed lines). Specifically, FIG. 7 shows the fragrance intensities generated over time by exemplary air fresheners shown in FIGS. 1-2 comprising both continuous passive delivery mechanism 3 and on-demand delivery mechanism 5. FIG. 8 shows the performance of an exemplary freshener according to FIGS. 3-5.

Describing, now, the performance of the present invention (solid line) shown in FIG. 7 from left to right, a first horizontal line indicates a generally constant, continuous passive delivery intensity. Next, an upward spike or peak characterizes an instantaneous fragrance burst release from an on-demand fragrance delivery mechanism. A downward slope following the peak characterizes the typical dissipation of instantaneous fragrance bursts. A second horizontal line, elevated with respect to the first horizontal line, shows the combined-effect interval of the first continuous passive release and the on-demand supplemental passive release. Finally, after a prolonged interval of combined effect intensity, prolonged being relative to the normal burst dissipation interval characterized earlier, a gradual downward slope indicates the eventual exhaustion of the on-demand passive reserves and return to the first continuous passive delivery intensity.

The continuous-burst prior art plot is characterized by a first constant continuous delivery intensity followed by an instantaneous burst and a downward dissipation slope, ultimately settling to the previous constant intensity. The burst-semi-continuous prior art plot is characterized by an initial instantaneous burst intensity followed by a downward slope representing the normal dissipation of airborne bursts. This is followed by a prolonged, semi-constant intensity ultimately tapering off to zero. The prior art plots are the same for FIGS. 7-8.

With particular reference to FIG. 8 and describing the solid line plot from left to right, a first generally horizontal line indicates a generally constant, continuous passive delivery intensity. Next, an upward slope characterizes the incremental fragrance release following activation of a supplemental on-demand fragrance delivery mechanism. A second horizontal line, elevated with respect to the first horizontal line, shows the combined-effect interval of the first continuous release and the supplemental on-demand passive release. Finally, after a prolonged interval of combined-effect intensity, a downward slope indicates the eventual exhaustion of the on-demand passive reserves and return to the first continuous delivery intensity.

The exemplary prolonged elevated intensity intervals in FIGS. 7-8 may be shortened or lengthened as a function of the configuration and design of the on-demand delivery mechanism. In FIG. 7, for example, respective interval lengths may depend on the amount of fragrance instantaneously released relative to that which is deposited for passive release upon activation of the on-demand delivery mechanism. In FIGS. 7-8, the rise between the first passive release intensity and the combined passive release intensity may depend on the respective dispersion capacities and reserves.

Finally, while the present invention has been described above with reference to various exemplary embodiments, many changes, combinations and modifications may be made to the exemplary embodiments without departing from the scope of the present invention. For example, the various components may be implemented in alternate ways. These alternatives can be suitably selected depending upon the particular application or in consideration of any number of factors associated with the operation of the system. In addition, the techniques described herein may be extended or modified for use with other types of devices. These and other changes or modifications are intended to be included within the scope of the present invention.

What is claimed is:

1. An integrated multiple delivery fragrance system comprising:
   a continuous delivery mechanism, delivering a first fragrance;
   an on-demand delivery mechanism for delivering periodic fragrance bursts of a second fragrance, said on-demand delivery system being adjacent to an emanator, wherein said on-demand delivery system is configured to directly deposit at least a portion of said fragrance bursts on said emanator for subsequent extended passive delivery.

2. The multiple delivery fragrance system of claim 1 wherein said on-demand delivery mechanism comprises a microsprayer.

3. The multiple delivery fragrance system of claim 1 wherein said first and second fragrances are drawn from a common reservoir.

4. The multiple delivery fragrance system of claim 1 wherein said first and second fragrances are drawn from different reservoirs.

5. The multiple delivery fragrance system of claim 4 wherein said separate reservoirs are at least one of independently refillable, independently replaceable, and jointly replaceable.

6. The multiple delivery fragrance system of claim 1 further comprising at least one of a heater, blower, fan, timer, intensity control, duration control and sensor.

7. The multiple delivery fragrance system of claim 1, wherein each of said first and second fragrances comprise at least one of an air freshener, deodorizer, odor eliminator, insecticide, insect repellant, medicine, disinfectant, sanitizer, mood enhancer and aroma therapy composition.

* * * * *